US011857759B2

(12) United States Patent
Shiau

(10) Patent No.: US 11,857,759 B2
(45) Date of Patent: Jan. 2, 2024

(54) SYSTEM FOR DETECTING AND REPORTING FLUID LEVELS IN AN INFUSION DEVICE

(71) Applicant: Parker Holding Services Corp., New Taipei (TW)

(72) Inventor: Vincent Shiau, Athens, GA (US)

( * ) Notice: Subject to any disclaimer, the term of this patent is extended or adjusted under 35 U.S.C. 154(b) by 251 days.

(21) Appl. No.: 17/109,061

(22) Filed: Dec. 1, 2020

(65) Prior Publication Data
US 2022/0168504 A1 Jun. 2, 2022

(51) Int. Cl.
*A61M 5/168* (2006.01)
*A61J 1/10* (2006.01)

(52) U.S. Cl.
CPC .............. *A61M 5/1684* (2013.01); *A61J 1/10* (2013.01); *A61M 2205/18* (2013.01); *A61M 2205/3306* (2013.01); *A61M 2205/3327* (2013.01); *A61M 2205/42* (2013.01)

(58) Field of Classification Search
CPC ..................... A61M 5/1684; A61M 2205/3306
See application file for complete search history.

(56) References Cited

U.S. PATENT DOCUMENTS

| | | | | |
|---|---|---|---|---|
| 3,992,706 A | * | 11/1976 | Tunney ............... | A61M 5/1684 604/245 |
| 4,378,014 A | * | 3/1983 | Elkow ................. | A61M 5/1684 604/245 |
| 4,984,462 A | * | 1/1991 | Hass, Jr .............. | G01F 23/2921 604/404 |
| 5,135,485 A | * | 8/1992 | Cohen .................. | G01F 23/268 604/67 |
| 2008/0252472 A1 | * | 10/2008 | Su ....................... | A61M 5/1684 340/619 |
| 2010/0134303 A1 | * | 6/2010 | Perkins ............... | A61M 5/1684 340/619 |
| 2014/0278156 A1 | * | 9/2014 | Thompson .......... | A61M 5/1684 235/375 |

FOREIGN PATENT DOCUMENTS

WO    WO-2017184777 A1 * 10/2017

* cited by examiner

*Primary Examiner* — Jenna Zhang

(74) *Attorney, Agent, or Firm* — Keith Kline; The Kline Law Firm

(57) ABSTRACT

This disclosure addresses a monitoring device for an infusion system. The device is typically used with an infusion device utilizing a clear reservoir bag holding the supplied fluid. The device uses light sources and sensors to accurately determine the level of the fluid, the amount of fluid being supplied, and when replenishment of the fluid is required. In addition, the device may utilize ultrasound sources and sensors as backups to the light system. The device further includes a data processing module that gathers, stores, and reports data relative to the fluid flow properties of the infusion device.

14 Claims, 5 Drawing Sheets

SYSTEM FOR DETECTING AND REPORTING FLUID LEVELS IN AN INFUSION DEVICE

CROSS REFERENCE TO RELATED APPLICATIONS

N/A

FIELD OF THE DISCLOSURE

The present disclosure relates generally to medical devices, and more particularly is a system for detecting and reporting fluid levels in an infusion device.

SUMMARY

Intravenous therapy is a common practice in hospital. It requires constant care and attention from medical personnel, typically nurses. Problems arise if the nurse on duty allows the infusion to run dry, or if the fluid in an infusion bag is not flowing steadily. According to statistics, more than 50% of the complaints from patients and their family is connected to issues related to infusion procedures. To prevent this, constant monitoring of the infusion system is necessary. This can represent a significant drain on manpower. A better monitoring design/device can facilitate a hospital's effort to reduce manpower by reducing the manpower required to monitor infusion processes. This is part of the overall effort to decrease human resources costs. Reducing the time required for monitoring tasks can also help medical personnel to pay more attention to other matters not as mundane as monitoring infusion, thereby increasing the efficiency of the nurses and providing better quality of services for patients.

In various embodiments of the present disclosure, a system adapted to monitor a fluid level in an infusion bag includes an infusion bag that holds a fluid to be supplied to a patient, at least one light source positioned on a first side of the infusion bag, at least two light sensors positioned on a second side of the infusion bag, and a control system including means to trigger the at least one light source, to receive signals from the light sensors, and to transmit information to reporting and warning modules. When fluid is present in a line of travel of light from the first light source, the light is diffracted and detected by a first one of the light sensors. When fluid is not present in the line of travel of light from the first light source, the light is not diffracted and is detected by a second one of the light sensors, the system thereby detecting a level of the fluid in the infusion bag.

BRIEF DESCRIPTION OF THE DRAWINGS

The accompanying drawings, wherein like reference numerals refer to identical or functionally similar elements throughout the separate views, together with the detailed description below, illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The present disclosure is directed to devices used to monitor fluid levels in infusion devices, to determine whether the devices are maintaining proper flow rates and when the reservoirs need to be replenished. The monitoring devices use light sources and light sensors to determine the physical boundaries of the fluid being dispensed.

Figure 1:
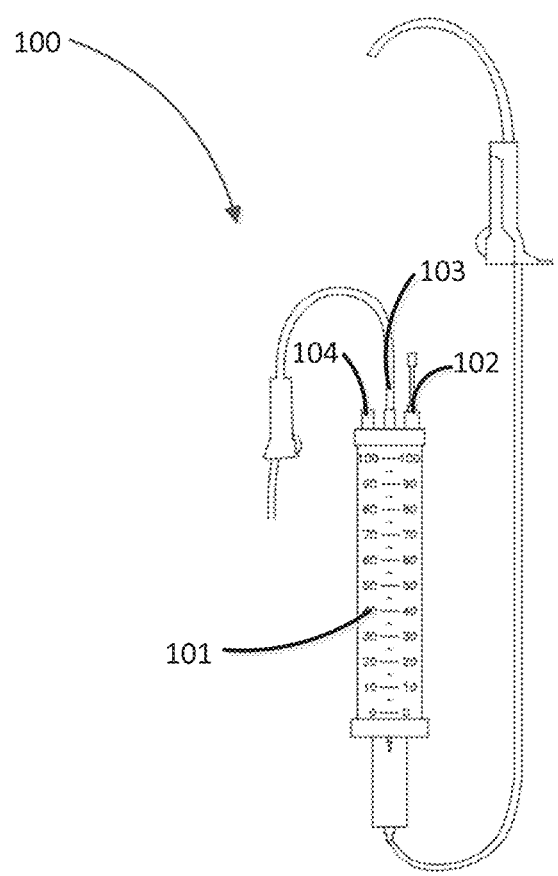
FIG. 1 depicts an infusion bag device according to various embodiments of the present invention.

Referring first to FIG. 1, a system 100 is configured to monitor and control a fluid level in an infusion bag 101. The infusion bag includes at an upper end of a main body an air vent 102, an inlet 103, and an injection port 104. The main body of the infusion bag 101 is typically formed from a flexible plastic. Preferably, materials adaptable to 3D printers are utilized. The bag may even be made from corn powder. Those skilled in the art will recognize that many materials are suitable for use in forming the infusion bag 101.

The air vent 102 provides a means for maintaining an appropriate air pressure in the body of the bag 100 so that fluid flow may occur properly. The inlet 103 provides the mechanism whereby the fluid being used in the infusion process is supplied to the infusion bag 100. The injection port 104 allows a caregiver to inject additional required fluids into the infusion bag 100.

Figure 2:
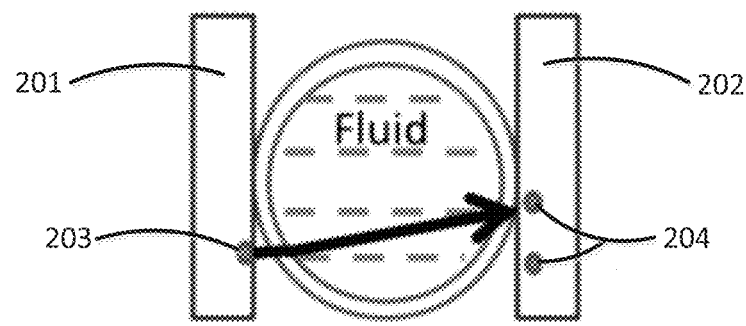
FIG. 2 shows one configuration of the infusion bag with light sources and monitoring sensors.

FIG. 2 illustrates the basic concept of the monitoring function of the infusion system. The infusion bag 101 is mounted between a light source mount 201 and a light sensor mount 202. The light source mount 201 includes at least one light source 203. The at least one light source 203 is positioned to direct light through the infusion bag 100. The light is detected by one of at least two light sensors 204. When fluid is present in the path of the light emitted from the light source 203, the light is refracted by the fluid, so that it is detected by a first one of the light sensors 204. If no fluid is present in the path of the emitted light, the light travels in a straight line and is detected by a second one of the light sensors 204. By this mechanism, the system, using a plurality of light sources and sensors, can detect and track when the fluid level drops past a certain point. The system then triggers a warning and/or a report that the fluid has reached certain level. (More about this function follows below.)

Figure 3:
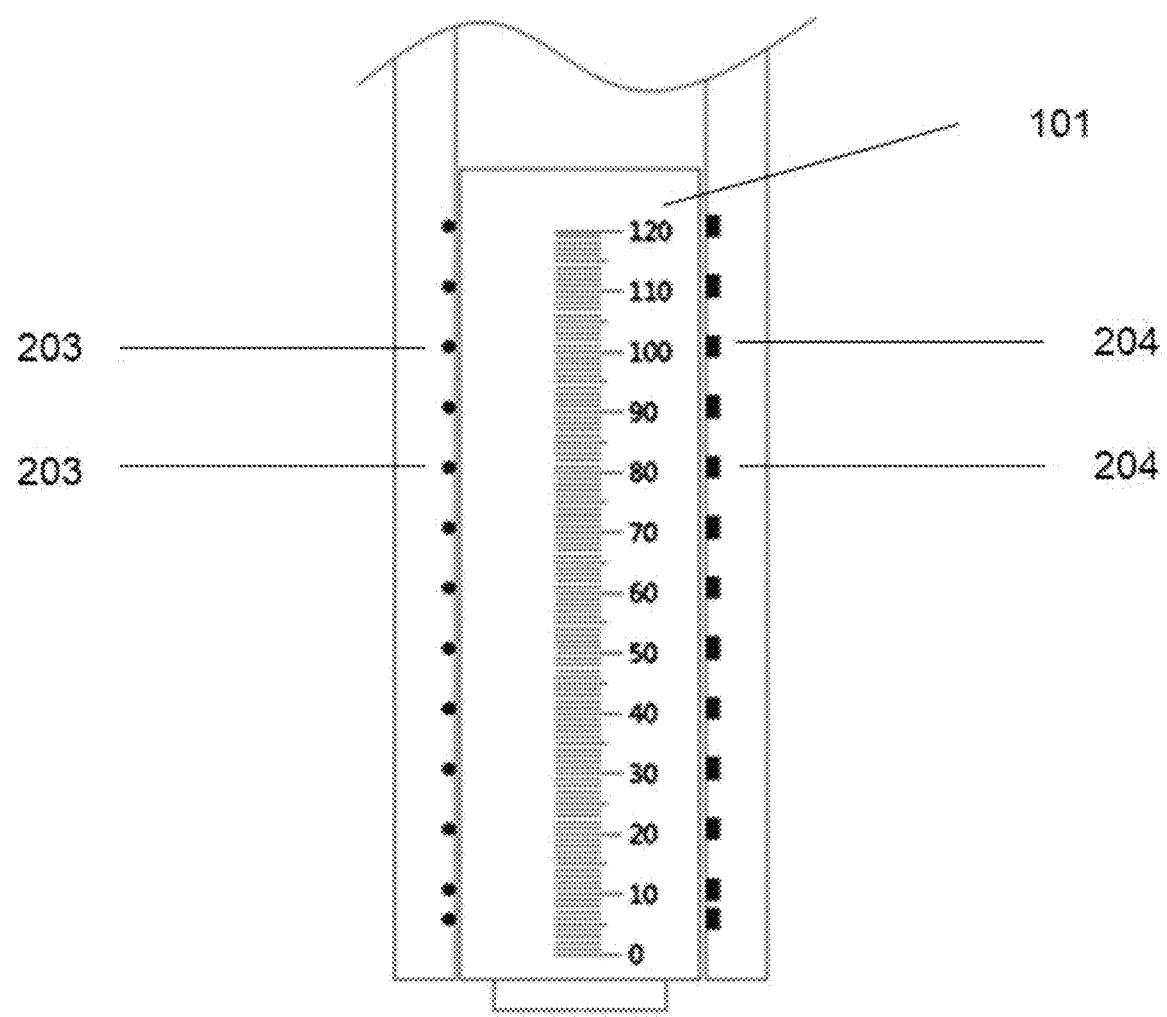
FIG. 3 illustrates another configuration of the infusion bag with light sources and monitoring sensors.

FIG. 3 shows another configuration for the sources and sensors of the system. It is important for the stationary system illustrated in FIG. 3 to have an array of light sources 203, and an array of light sensors 204. The light sources 203 are positioned on a first side of the infusion bag 101. As the fluid level in the bag 101 drops, successive light sensors 204 will be activated. As each successive sensor 204 in the array is activated, the system detects and reports the drop of the fluid level in the infusion bag 101. When the lowermost sensor 204 is activated, the system recognizes that the fluid needs to be replenished, and reports this situation to those individuals (generally nurses) monitoring the system 100. The report may be in the form of a text message, a visual alert (graphic or text) on a monitor of the system, and/or an audible alarm.

Figure 4:
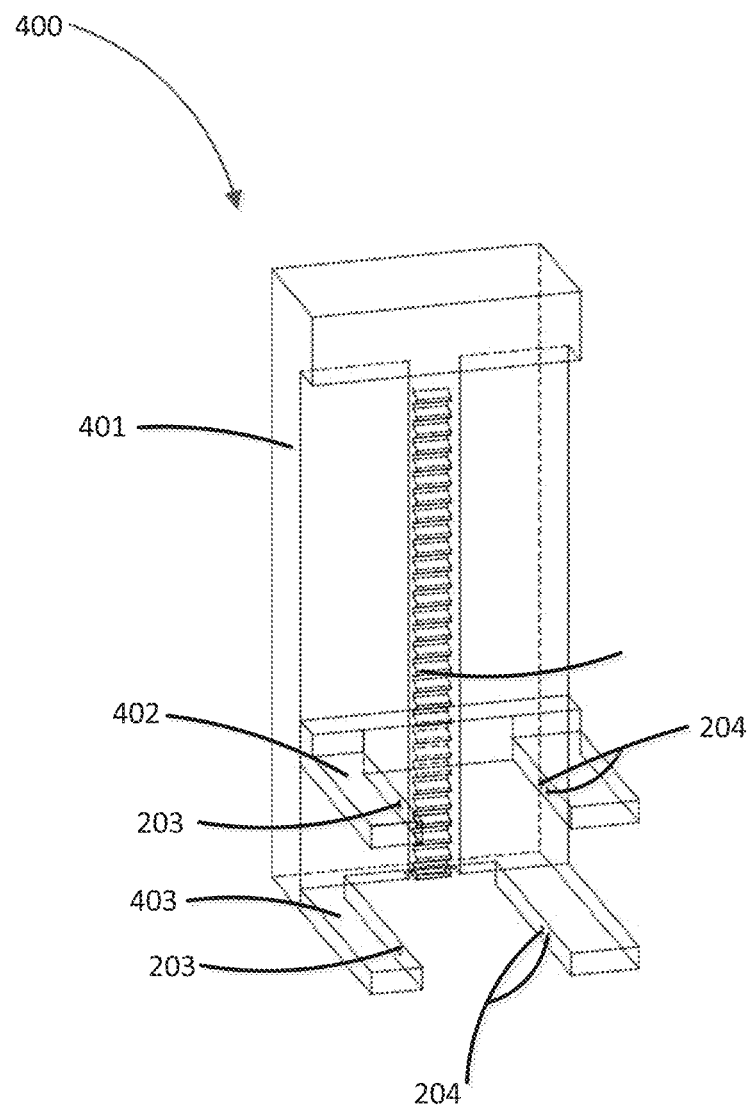
FIG. 4 shows an infusion bag with a movable mounting device for the light sources and sensors.

FIG. 4 shows a system 400 that employs a light bracket 401 with a movable arm 402. The arm 402 moves up and down within the light bracket 401, thereby changing the position of the light source/sensor pairs on the movable arm 402. When the movable arm 402 reaches the bottom of its travel path, the system 400 recognizes that the fluid in the infusion bag 101 needs replenished, and reports the situation. Again, the report may be in the form of a text message, a visual alert (graphic or text) on a monitor of the system, and/or an audible alarm. Those skilled in the art will recognize that a plethora of mechanical systems may be utilized to move the light source/sensor pairs up and down within the expanse of the infusion bag 101. Any such mechanism that allows the light source/sensor pairs to traverse the height of the infusion bag 101 will suffice. The system 400 will in various embodiments include a stationary base 403 that also includes at least one light source 203 and at least two light sensors 204. The base 403 allows convenient monitoring of the bottom of the infusion bag 101, where the fluid level is critical.

An additional benefit to the system depicted in FIG. 4 is that the movement of the arm 402 can be used to physically trigger an alarm for the system as a backup to the light source and sensors that serve as the main detection mechanism. A contact switch positioned at or near the bottom of the bracket 401 may be triggered when the arm reaches the bottom of its travel path, thereby activating whatever alarm means have been chosen by the users. The duplicative detecting mechanisms make the system far more reliable than a system with only one mechanism, nearly foolproof.

Figure 5:
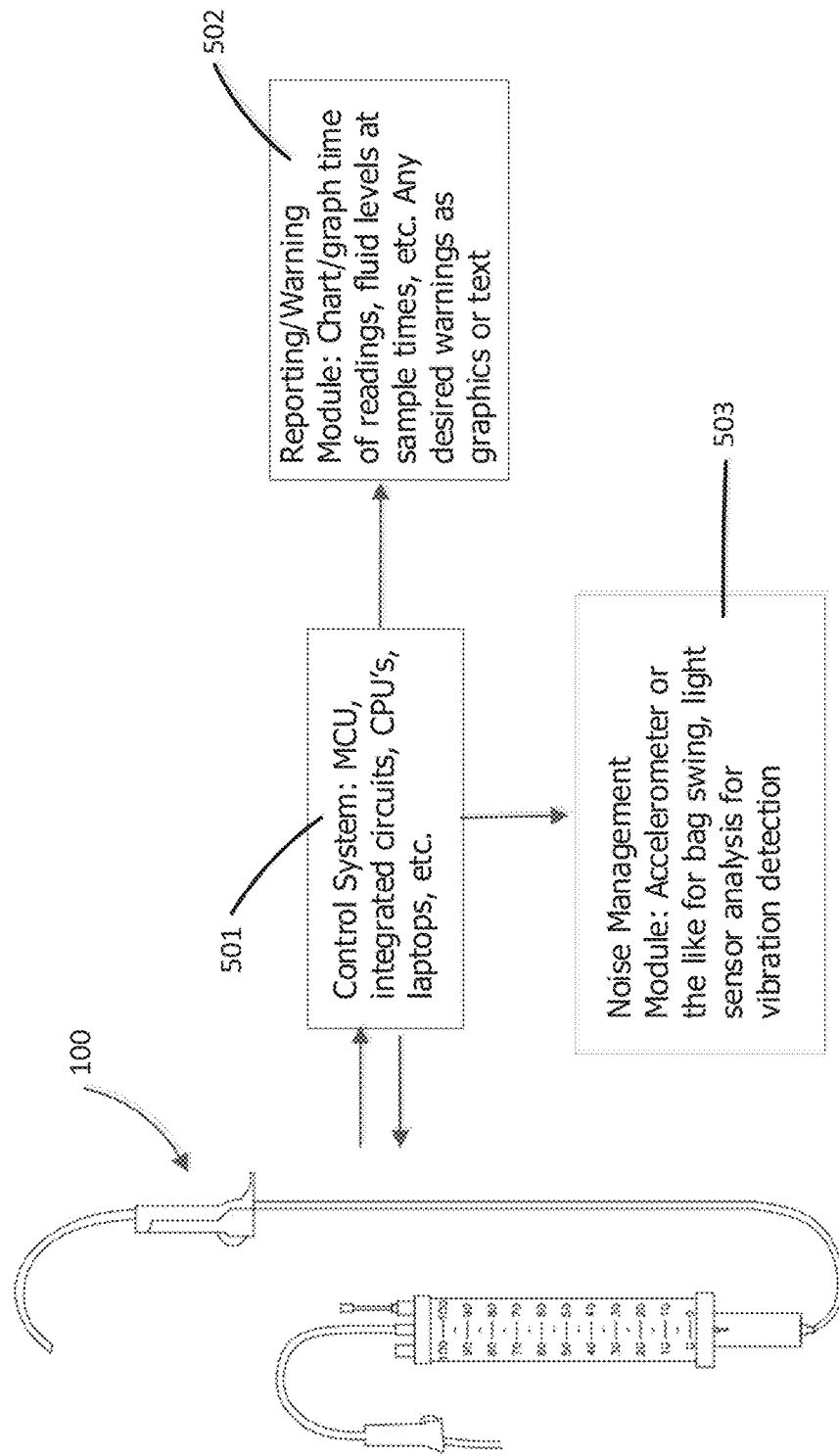
FIG. 5 is a graphical depiction of the system.

FIG. 5 is a schematic of the overall system for detecting and reporting fluid levels in an infusion device 100. The light sources 203 and light sensors 204 are in two-way communication with a control system 501. It is envisioned that in most installations of the system 100, the control system 501 will be an integral part of an MCU (multipoint control unit) of a medical facility in which the system is installed. The control system 501 may include integrated circuits, CPU's, laptops, or any other kind of data processing system as may be chosen by the users. In various embodiments, the light sources 203 and sensors 204 are controlled by and send data via a wireless IOT (Internet of Things) network.

Once data relative to the fluid level in the infusion bag is received in the control system 501, whatever reporting is desired is available through a reporting module 502. The reporting module 502 can generate time/fluid level date for each of the bags being utilized in the system. The reports, and particularly any warnings generated, can be monitored by the appropriate personnel, e.g. nurses. The nurses can receive the reports and warnings via any smart device, such as their phone, or a laptop or desk computer. The warning are triggered by predetermined conditions, such as fluid level, motion detected within the system, malfunction of hardware, etc. The reporting module can also trigger whatever alarms are desired within the system. Audible alarms, graphics, and written messages are all options.

If desired by the user, a noise management module 503 may be installed in the system. Available options for the noise management module include means to detect motion of the bag unit itself, such as installing an accelerometer in physical contact with the bag itself. Those skilled in the art can envision multiple other methods of detecting motion in the bag. In a medical setting, two things can happen that interfere with the readings of the fluid level in the bag. First, patients or their family may touch the infusion device. This can lead to a large angle swing or motion of the infusion bag 101. The infusion bag 101 should not have any acceleration, as any acceleration can interfere with the readings obtained from the light sensors 204. The second phenomenon is that a small vibration generated due to movement of the patient may lead to vibration of the fluid in the drip bag. Since the methodology of the system relies on determining refraction through the fluid, movement of the fluid surface caused by a small amount of vibration of the fluid surface can lead to inaccurate readings from the light sensors 204.

Therefore, in the case of significant movement, the system can utilize the accelerometer readings to enable the system to rule out false readings due to movement of the device.

For the second case of minor movement, a small vibration may lead to vibration in the light sources 203 and the light sensors 204. If more than one light sensor 204 receives a signal from a given light source 203, the system knows that this signal is due to movement of the device. The signal can therefore be discarded, and if desired, recorded in the reporting module 502. An alarm may also be generated. These procedures, using devices such as an accelerometer and monitoring for false signals from the light sensors 204, provide a method for the system to cross check and verify the signals received from the light sensors 204.

The technology disclosed herein addresses improved monitoring systems for fluid infusion devices.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present disclosure. As such, some of the components may have been distorted from their actual scale for pictorial clarity.

In the foregoing description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A system adapted to monitor a fluid level in an infusion bag, comprising:
   an infusion bag that holds a fluid to be supplied to a patient,
   at least one light source positioned on a movable element at first side of the infusion bag,
   at least two light sensors positioned on the movable element at a second side of the infusion bag,
   a control system including means to trigger the at least one light source, to receive signals from the at least two light sensors, and to transmit information to reporting and warning modules;
   wherein when fluid is present in a line of travel of light from the at least one light source, the light is diffracted and detected by a first one of the at least two light sensors, and
   when fluid is not present in the line of travel of light from the at least one light source, the light is not diffracted and is detected by a second one of the light sensors, the system thereby detecting a level of the fluid in the infusion bag, and
   when the movable element reaches an end of its travel path, an alarm is triggered to alert the personnel monitoring the system to the fluid level.

2. The system of claim 1, wherein:
   the control system is in communication with a reporting and warning module.

3. The system of claim 2, wherein:
   the reporting and warning module generates reports regarding the overall system performance, and triggers warnings for personnel monitoring the system when predetermined conditions occur.

4. The system of claim 1, wherein:
   the control system is in communication with a noise management module.

5. The system of claim 4, wherein:
   the noise management module mitigates difficulties caused by extraneous factors.

6. The system of claim 4, wherein:
   the noise management module analyzes a signal from an accelerometer to determine if the infusion bag is moving.

7. The system of claim 4, wherein:
   the noise management module analyzes signals from the light sensors to determine if a vibration has affected the detection of the fluid level.

8. A system adapted to monitor a fluid level in an infusion bag, comprising:
   an infusion bag that holds a fluid to be supplied to a patient,
   at least one light source positioned on a first side of the infusion bag,
   at least two light sensors positioned on a second side of the infusion bag,
   a control system including means to trigger the at least one light source, to receive signals from the at least two light sensors, and to transmit information to reporting and warning modules; wherein
   the at least one light source and the at least two light sensors are positioned on a movable element, and
   when fluid is present in a line of travel of light from the at least one light source, the light is diffracted and detected by a first one of the light sensors, and
   when fluid is not present in the line of travel of light from the at least one light source, the light is not diffracted and is detected by a second one of the light sensors, the system thereby detecting a level of the fluid in the infusion bag, and
   when the movable element reaches an end of its travel path, an alarm is triggered to alert personnel monitoring the system to the fluid level.

9. The system of claim 8, wherein:
   the control system is in communication with a reporting and warning module.

10. The system of claim 9, wherein:
    the reporting and warning module generates reports regarding the overall system performance, and triggers warnings for personnel monitoring the system when predetermined conditions occur.

11. The system of claim 8, wherein:
    the control system is in communication with a noise management module.

12. The system of claim 11, wherein:
    the noise management module mitigates difficulties caused by extraneous factors.

13. The system of claim 11, wherein:
the noise management module analyzes a signal from an accelerometer to determine if the infusion bag is moving.

14. The system of claim 11, wherein:
the noise management module analyzes signals from the light sensors to determine if a vibration has affected the detection of the fluid level.

* * * * *